US006800491B2

(12) United States Patent
Ringleben et al.

(10) Patent No.: US 6,800,491 B2
(45) Date of Patent: Oct. 5, 2004

(54) ROBOTIC RESERVOIR WITHOUT LIQUID HANGUP

(75) Inventors: Ronald D. Ringleben, Fairport, NY (US); Ian Pratt, Alfred Station, NY (US)

(73) Assignee: Nalge Nunc International Corporation, Rochester, NY (US)

( * ) Notice: Subject to any disclaimer, the term of this patent is extended or adjusted under 35 U.S.C. 154(b) by 381 days.

(21) Appl. No.: 09/877,164

(22) Filed: Jun. 8, 2001

(65) Prior Publication Data
US 2002/0187079 A1 Dec. 12, 2002

(51) Int. Cl.$^7$ .................................................. B01L 3/00
(52) U.S. Cl. ...................... 436/180; 422/100; 422/102; 435/288.4; 435/288.5; 435/305.2
(58) Field of Search ................... 422/100, 102; 436/180; 435/288.3, 288.4, 288.5, 305.1, 305.2

(56) References Cited

U.S. PATENT DOCUMENTS

| | | | | |
|---|---|---|---|---|
| 3,190,731 | A | 6/1965 | Weiskopf | 23/292 |
| D226,846 | S | 5/1973 | Rosenburg | D16/1 |
| 4,154,795 | A | 5/1979 | Thorne | 422/99 |
| 4,545,958 | A | 10/1985 | Dopatka | 422/102 |
| 4,599,315 | A | 7/1986 | Terasaki et al. | 435/301 |
| 4,720,374 | A | 1/1988 | Ramachandran | 422/310 |
| 4,735,778 | A | 4/1988 | Maruyama et al. | 422/102 |
| 4,770,856 | A | 9/1988 | Uthemann et al. | 422/104 |
| 4,948,442 | A | 8/1990 | Manns | 156/73.1 |
| 4,956,150 | A | 9/1990 | Henry | 422/102 |
| 5,009,942 | A | 4/1991 | Benin et al. | 422/102 |
| 5,180,555 | A | 1/1993 | Monget | 422/102 |
| 5,229,163 | A | 7/1993 | Fox | 427/2 |
| 5,272,084 | A | * 12/1993 | O'Connell et al. | 435/395 |
| 5,456,360 | A | 10/1995 | Griffin | 206/443 |
| 5,472,672 | A | 12/1995 | Brennan | 422/131 |
| 5,603,899 | A | 2/1997 | Franciskovich et al. | 422/100 |
| 5,989,499 | A | 11/1999 | Catanzariti et al. | 422/63 |
| 6,027,695 | A | 2/2000 | Oldenburg et al. | 422/102 |
| 6,083,761 | A | * 7/2000 | Kedar et al. | 436/178 |
| 6,143,250 | A | 11/2000 | Tajima | 422/102 |
| 6,180,065 | B1 | * 1/2001 | Homola | 422/102 |
| 6,309,889 | B1 | 10/2001 | Cutler et al. | 436/165 |
| 6,432,365 | B1 | * 8/2002 | Levin et al. | 422/100 |

FOREIGN PATENT DOCUMENTS

| | | |
|---|---|---|
| CH | 673964 | 4/1990 |
| DE | 4405375 A1 | 8/1995 |

(List continued on next page.)

OTHER PUBLICATIONS

Tomtec. Inc., Reagent Reservoirs Quadra96 Accessory, http://www.tomtec.com/Pages/CustomReservoir.html, as of Feb. 12, 2001.

(List continued on next page.)

Primary Examiner—Jan M. Ludlow
(74) Attorney, Agent, or Firm—Wood, Herron & Evans, LLP

(57) ABSTRACT

A reagent reservoir with a patterned bottom for full extraction of a liquid reagent by a multiple head pipettor. The bottom wall includes a plurality of recesses, each corresponding to a head of a multiple head pipettor. Each recess opens upwardly to receive the pipettor head, and includes a top edge, a bottom and surrounding side wall portions that angle outwardly from the recess bottom to the top edge. The recesses promote flow of the liquid reagent to the recess bottoms and prevent liquid hangup between recesses to eliminate waste of the liquid reagent. In one exemplary embodiment of the present invention, the top edges between adjacent recesses meet at an angle to form a pointed peak.

15 Claims, 3 Drawing Sheets

FOREIGN PATENT DOCUMENTS

| | | |
|---|---|---|
| DE | 4424112 A1 | 1/1996 |
| DE | 19541980 A1 | 4/1996 |
| DE | 4446698 A1 | 6/1996 |
| EP | 0106662 A2 | 4/1984 |
| EP | 0542422 A1 | 5/1993 |
| EP | 0816827 A2 | 1/1998 |
| GB | 2181843 | 4/1987 |
| JP | 61-215947 | 9/1986 |
| JP | 2-296151 | 12/1990 |
| WO | WO/87/03218 | 6/1987 |
| WO | WO 91/06368 | 5/1991 |
| WO | WO 94/13402 | 6/1994 |
| WO | WO 94/21379 | 9/1994 |
| WO | WO 94/28111 | 12/1994 |
| WO | WO 96/36436 | 11/1996 |
| WO | WO 98/28075 | 7/1998 |

OTHER PUBLICATIONS

Robbins Scientific, *Molecular Biology: PCR Plastics*, http://www.robsci.com/PCR/vgroove.html, as of Feb. 8, 2001.

ICN Biomedicals, *Diagnostic Instruments & Reagents*, Brochure, 2 pgs., May 1992/1993.

Stuart G. Reeves et al., *Investigation of a Novel Microtiter Plate Support Material and Scanner Quantitation of Immunoassays, Proteins and Phospholipids*, Article, 16 pgs. 1993.

* cited by examiner

ROBOTIC RESERVOIR WITHOUT LIQUID HANGUP

FIELD OF THE INVENTION

This invention relates to a reservoir for containing reagent to be extracted and pipetted into multi-well test plates.

BACKGROUND OF THE INVENTION

Multi-well test plates are well known in scientific areas, such as biotechnology, for allowing the detection and measurement of substances present in translucent liquid samples. Generally, this is accomplished by measuring the light absorbence characteristics of the sample through one or more spectroscopy procedures. Typically, a framework of test wells is opened at the top for receiving the liquid samples, and is closed with a transparent bottom for allowing light radiation penetration in a wavelength region necessary for a particular study. These studies, commonly referred to as assays, may include drug concentration assays, drug metabolite assays, enzyme activity assays, enzyme cofactor assays, fluorescent probe excitations or emissions, DNA spectral shifts or DNA and protein concentration measurements, as well as many other studies. The well plates typically consist of a plurality of individual wells configured so that an aliquot of a sample may be placed within each well. The wells are typically arranged in relatively close proximity in a matrix pattern, allowing samples to be studied individually or as a group. Common sizes for microplates include matrices having dimensions of 4×6 (24 wells), 8×12 (96 wells), or 16×24 (384 wells), although larger well plates are also used that may include matrices of hundreds or even thousands of wells.

Prior to filling the well plates with reagent for carrying out the desired reaction and/or tests, a desired quantity of reagent is measured out into a reservoir. For example, if each well in a 96 well plate needs 1 milliliter of reagent for carrying out the measurement or reaction, a minimum of 96 milliliters of reagent is needed in the reservoir. A multiple head pipettor, in this case a 96 well pipettor head format, is used to extract the reagent for filling of the 96 wells. However, flat bottomed reservoirs or patterned bottoms with raised flat areas result in liquid hangup such that a portion of the liquid reagent is not positioned to be extracted into one of the heads of the multiple head pipettor. Thus, an additional amount of reagent is required to be added to the reservoir to account for the fact that some reagent will be wasted due to the design of the reservoir bottom. The reagents used for many of the assays are very expensive or precious, such that even small amounts of waste are unacceptable.

There is thus a need to provide a reagent reservoir and method for liquid reagent extraction that allows for full extraction of the liquid reagent therein by a multiple head pipettor.

SUMMARY OF THE INVENTION

The present invention provides a reagent reservoir with a patterned bottom that allows full extraction of a liquid reagent by a multiple head pipettor, and a method of using the reservoir. To this end, and in accordance with the present invention, the reservoir is provided having side walls and a bottom wall for containing the liquid reagent, wherein the bottom wall includes a plurality of recesses, each corresponding to a head of the multiple head pipettor. Each recess opens upwardly to receive the pipettor head, and includes a top edge, a bottom and surrounding side wall portions that angle outwardly from the recess bottom to the top edge. The recesses promote flow of the liquid reagent to the recess bottoms and prevent liquid hangup between recesses to eliminate waste of the liquid reagent. In one exemplary embodiment of the present invention, the surrounding side wall portions include four connected substantially triangular surfaces that angle outwardly from the recess bottom. In another exemplary embodiment of the present invention, the top edges between adjacent recesses meet at an angle to form a pointed peak. In using the reservoir, the interior of the reagent reservoir is filled with a desired volume of liquid reagent, the pipettor is positioned such that each pipettor head is aligned with a respective recess bottom, and the reagent is extracted. By virtue of the patterned bottom, substantially complete to full extraction of the reagent may be achieved.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain one illustrative embodiment of the invention.

DETAILED DESCRIPTION

Figure 1:
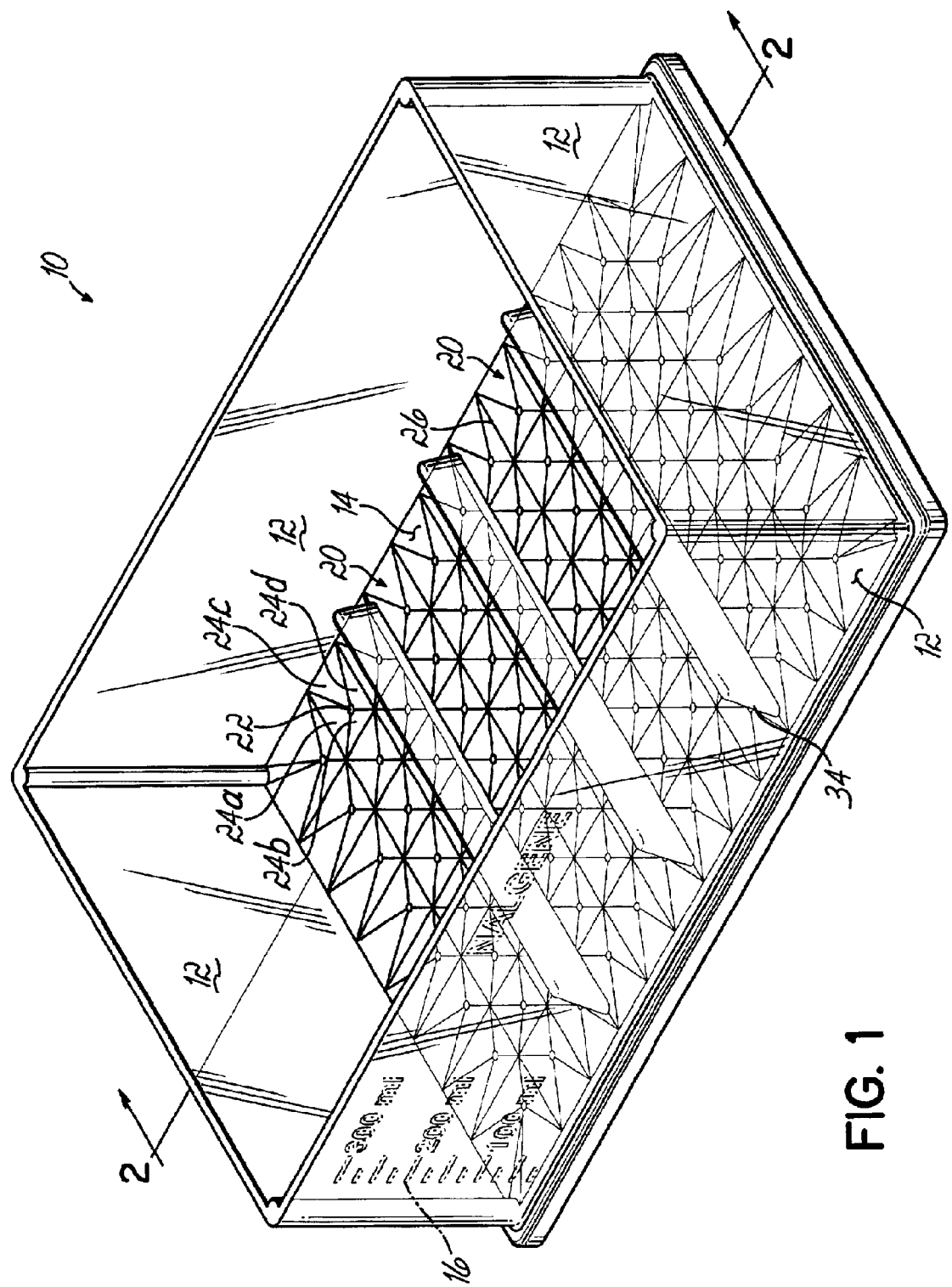
FIG. 1 is a perspective view of a reagent reservoir of the present invention.
Figure 2:
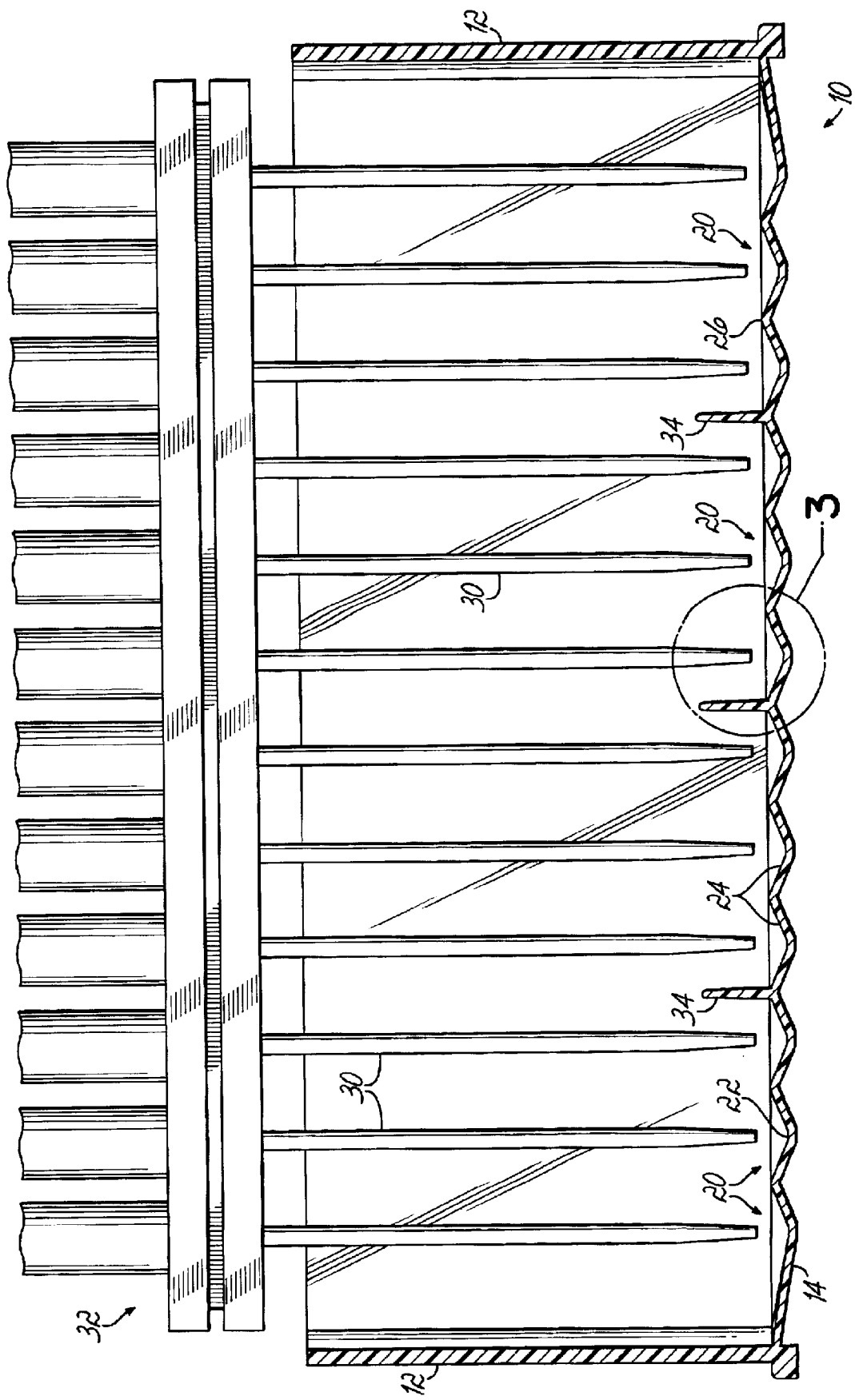
FIG. 2 is a cross-sectional view along line 2—2 of FIG. 1, further depicting a multiple head pipettor positioned to extract liquid reagent from the reservoir of the present invention.
Figure 3:
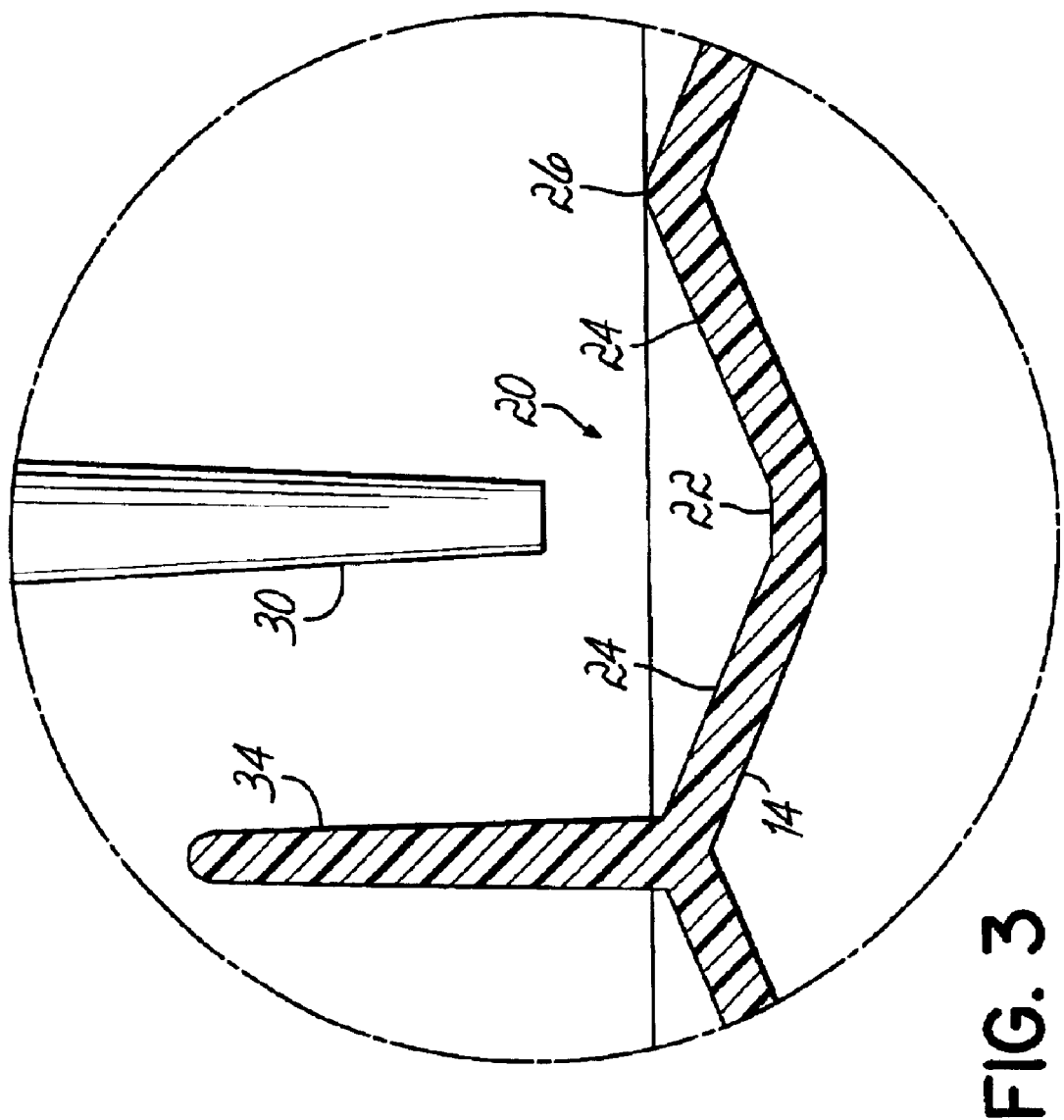
FIG. 3 is an enlarged view of area 3 of FIG. 2 depicting a recess in the patterned bottom of the reservoir of the present invention.

Referring to FIGS. 1–3, a reagent reservoir 10 constructed in accordance with one exemplary embodiment of the invention generally comprises a plurality of side walls 12 and a bottom wall 14, which collectively define an interior for containing a liquid reagent. The reagent reservoir 10 is preferably formed from a polymer, such as polypropylene or polystyrene, and is preferably opaque. The reagent reservoir 10 depicted in FIG. 1 includes measuring indicia 16 to enable accurate measurement of a quantity of liquid reagent therein. Specifically, the reservoir depicted in FIG. 1 allows for accurate measurement of up to 300 milliliters of liquid reagent. It is to be understood, however, that the depth of the reservoir 10 may be lesser or greater than that depicted, depending on the needs of the particular experiments or assays to be conducted.

Bottom wall 14 includes a plurality of recesses 20 into which the liquid reagent settles upon being measured into the reagent reservoir 10. Each recess 20 opens upwardly to receive one of the heads 30 of a multiple head pipettor 32, as depicted in FIG. 2. The particular embodiment depicted in FIGS. 1–3 includes a bottom wall 14 having 96 recesses 20, each recess 20 opening upwardly to receive one of the 96 heads 30 of a 96 well pipettor head format. It should be understood, however, that the reagent reservoir 10 of the present invention may contain any number of recesses 20 to correspond to different pipettor head formats. For example, pipettor head formats are provided for 384 well test plates, 1,536 well test plates, and so forth.

Each recess 20 includes a bottom 22 and surrounding side wall portions 24 that angle outwardly from the bottom 22 to a top edge 26. The surrounding side wall portions 24 angle outwardly to the top edge 26 that either meets at an angle with a side wall 12 of the reservoir 10 or with a top edge 26 of an adjacent recess 20. The top edge 26 between adjacent recesses 20 advantageously forms a pointed peak which prevents liquid hangup between recesses 20. Alternatively, top edge 26 could be rounded. The liquid reagent is caused to flow downwardly to the recess bottoms 22 where the liquid reagent may be fully extracted by a respective head 30 of the multiple head pipettor 32, as depicted most clearly in FIG. 2. The prevention of liquid reagent hangup becomes important when the level of reagent in the reagent reservoir falls below the level of the top edges 26 of recesses 20.

As best shown in FIG. 1, each recess 20 may include a circular bottom 22, corresponding to the circular geometry of the heads 30 of the multiple head pipettor 32. To eliminate flat portions within the bottom wall 14 of the reservoir 10 that can cause liquid hangup, the recesses 20 may include surrounding side wall portions 24 comprising four connected substantially triangular surfaces 24a–d angling outwardly to the top edge 26. Top edge 26 would thus have a square or rectangular geometry defining the opening of recess 20. Recesses 20, in this embodiment, would thereby have an inverted pyramid-like configuration, such that no flat areas comprise the bottom wall 14, except for the bottom 22 of each recess 20. Bottoms 22, however, are not limited to flat surfaces. Top edges 26 between recesses 20 preferably meet in a peak, but could be rounded. In this embodiment, reagent is forced to flow down side walls 24 toward bottoms 22, and no liquid hangup can occur on top edges 26. Moreover, by virtue of including a plurality of such recesses 20 corresponding to the number of heads 30 in the pipettor 32, the liquid reagent is concentrated within the bottom wall 14 at the exact locations where the heads 30 will be positioned for extraction, ensuring that no reagent is wasted between adjacent pipettor heads 30.

In the embodiment shown in FIGS. 1–3, the reagent reservoir 10 includes a plurality of baffles 34 positioned between rows of recesses 20. These baffles 34 are optional, but when included, reduce splashing of the liquid reagent during filling, particularly for low volumes of reagent. The baffles preferably include an angled top portion 36 to further prevent liquid hangup within the interior of reservoir 10.

As best shown in FIGS. 1 and 2, side walls 12 have a height that is at least several times the depth of the recesses 20. The depth of the recesses 20 may be measured from the top edge 26 to the bottom 22. As a result, the interior of reservoir 10 has a volume that is substantially greater than the collective volume of the recesses 20 such that the liquid reagent can fill the reservoir to a level above the top edges 26 of the recesses 20.

In use, the reagent reservoir 10 is filled with a desired volume of liquid reagent. Advantageously, reservoir 10 is filled to a level substantially above the top edges 26 of the recesses 20, and more advantageously, to a volume that is at least several times greater than the combined volume of the recesses 20. Multiple head pipettor 32 is positioned, for example as shown in FIG. 2, with each pipettor head 30 aligned over a respective recess bottom 22. The liquid reagent is then extracted. The extraction may continue until all or substantially all of the liquid reagent is removed from the interior of the reagent reservoir 10. By virtue of the angled pattern of the bottom wall 14, the liquid reagent is caused to flow toward the recess bottoms 22 thereby enabling the complete or nearly complete extraction.

While the present invention has been illustrated by the description of embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A reagent reservoir for containing a liquid reagent, the reservoir comprising:

a plurality of reservoir side walls and a patterned bottom wall collectively defining a reservoir interior for containing the liquid reagent; and a plurality of recesses in the patterned bottom wall collectively surrounded by the reservoir side walls, the volume of the reservoir interior being substantially greater than the collective volume of the recesses, each recess facing upwardly, and each recess including a top edge, bottom, and a plurality of side wall portions, said side wall portions collectively surrounding said bottom wherein the side wall portions include four connected substantially triangular surfaces angling outwardly from the bottom to the top edge thereby promoting flow of the liquid reagent to the respective recess bottoms to allow full extraction of the liquid reagent, wherein the height of the reservoir side walls is at least several times the depth of the recesses in the patterned bottom wall so that liquid reagent can fill the reservoir to a level above the top edges of the recesses.

2. The reservoir of claim 1 comprising 96 recesses adapted to correspond to a 96 well pipettor head format.

3. The reservoir of claim 1 comprising 384 recesses adapted to correspond to a 384 well pipettor head format.

4. The reservoir of claim 1 comprising 1536 recesses adapted to correspond to a 1536 well pipettor head format.

5. The reservoir of claim 1 further comprising at least one baffle extending upward from the patterned bottom wall to reduce splashing of liquid reagent in the reservoir.

6. The reservoir of claim 1, wherein the top edges between adjacent recesses meet at an angle to form a pointed peak to thereby prevent liquid reagent from settling between recesses.

7. The reservoir of claim 1, wherein the recess bottoms are circular.

8. The reservoir of claim 1, wherein the top edges are rounded.

9. A reagent reservoir for containing a liquid reagent, the reservoir comprising:

a plurality of reservoir side walls and a patterned bottom wall collectively defining a reservoir interior for containing the liquid reagent; and a plurality of recesses in the patterned bottom wall collectively surrounded by the reservoir side walls, the volume of the reservoir interior being substantially greater than the collective volume of the recesses, each recess facing upwardly, and each recess including a top edge, a bottom, and four connected substantially triangular surfaces angling outwardly from the bottom to the top edge, wherein the top edges between adjacent recesses meet at an angle to form a pointed peak thereby promoting flow of the liquid reagent to the respective recess bottoms to allow full extraction of the liquid reagent, wherein the height of the reservoir side walls is at least several times the depth of the recesses in the patterned bottom wall so that liquid reagent can fill the reservoir to a level above the top edges of the recesses.

10. The reservoir of claim 9 comprising 96 recesses adapted to correspond to a 96 well pipettor head format.

11. The reservoir of claim 9 comprising 384 recesses adapted to correspond to a 384 well pipettor head format.

12. The reservoir of claim 9 comprising 1536 recesses adapted to correspond to a 1536 well pipettor head format.

13. The reservoir of claim 9, wherein the recess bottoms are circular.

14. The reservoir of claim 9 further comprising at least one baffle extending upward from the patterned bottom wall to reduce splashing of liquid reagent in the reservoir.

15. A method of extracting a liquid reagent from a reagent reservoir by a multiple head pipettor, the reservoir including a plurality of reservoir side walls and a patterned bottom wall collectively defining a reservoir interior, and a plurality of recesses in the patterned bottom wall, each recess facing upwardly to receive one of the heads of the pipettor, and each recess including a top edge, a bottom, and a plurality of side wall portions, said side wall portions collectively surrounding said bottom, and wherein the side wall portions include four connected substantially triangular surfaces angling outwardly from the bottom to the top edge, the volume of the reservoir interior being substantially greater than the collective volume of the recesses and the height of the reservoir side walls being at least several times the depth of the recesses in the patterned bottom wall so that liquid reagent can fill the reservoir to a level above the top edge of the recesses, the method comprising the steps of:

filling the interior of the reagent reservoir with the liquid reagent to a desired volume which is at a level substantially above the top edges of the recesses;

positioning the multiple head pipettor in the reservoir interior to align each pipettor head with a respective recess bottom; and repeatably extracting a sample volume of the liquid reagent from the reservoir interior using the multiple head pipettor until the liquid reagent is at least substantially completely removed from the reagent reservoir, said liquid reagent being accumulated at the bottoms of the respective recesses as the level of the liquid reagent falls below the top edge of the recesses, thereby facilitating further extraction by the pipettor heads aligned with the recess bottoms.

* * * * *